United States Patent [19]

Martin

[11] Patent Number: 4,518,536
[45] Date of Patent: * May 21, 1985

[54] COMPOSITIONS, WHICH PROMOTE PLANT GROWTH AND PROTECT PLANTS, BASED ON OXIME ETHERS AND OXIME ESTERS

[75] Inventor: Henry Martin, Allschwil, Switzerland

[73] Assignee: Ciba-Geigy Corporation, Ardsley, N.Y.

[*] Notice: The portion of the term of this patent subsequent to Oct. 12, 1999 has been disclaimed.

[21] Appl. No.: 430,059

[22] Filed: Sep. 30, 1982

Related U.S. Application Data

[62] Division of Ser. No. 129,499, Mar. 11, 1980, Pat. No. 4,466,822, which is a division of Ser. No. 881,953, Feb. 27, 1978, abandoned.

[30] Foreign Application Priority Data

Mar. 2, 1977 [CH] Switzerland ............ 2606/77
Feb. 8, 1978 [CH] Switzerland ............ 1348/78

[51] Int. Cl.³ ........................... C07C 121/66
[52] U.S. Cl. ............................... 260/465 D
[58] Field of Search ................... 260/465 D

[56] References Cited

U.S. PATENT DOCUMENTS

| | | | |
|---|---|---|---|
| 2,535,876 | 12/1950 | Stewart | 71/2.5 |
| 2,844,578 | 7/1958 | Acker | 260/256.5 |
| 3,492,333 | 1/1970 | Dickore et al. | 260/472 |
| 3,821,261 | 6/1974 | Kaugars | 260/347.7 |
| 3,868,244 | 2/1975 | Taylor et al. | 71/76 |
| 3,923,491 | 12/1975 | O'Brien et al. | 71/76 |
| 4,061,764 | 12/1977 | Crovetti | 424/275 |
| 4,353,736 | 10/1982 | Martin | 71/105 |

FOREIGN PATENT DOCUMENTS

| | | |
|---|---|---|
| 2436655 | 2/1975 | Fed. Rep. of Germany . |
| 1090986 | 11/1967 | United Kingdom . |
| 1101785 | 1/1968 | United Kingdom . |
| 1138057 | 12/1968 | United Kingdom . |

*Primary Examiner*—Nicky Chan
*Attorney, Agent, or Firm*—Edward McC. Roberts; Frederick H. Rabin

[57] ABSTRACT

Novel oxime ethers and oxime esters of the formula I given herein have various advantageous effects with regard to stimulation of plant growth, particularly in the early stage of development of the plant. Furthermore, such compounds have the property of rendering, in the sense of an antidote action, agricultural chemicals which would otherwise damage the plants (phytotoxic chemicals) more compatible with the cultivated plants. Herbicides that are insufficiently selective can be used for example in the presence of such oxime derivatives in specific cultivated crops for combating weeds, without disadvantageous consequences for the cultivated plants.

6 Claims, No Drawings

COMPOSITIONS, WHICH PROMOTE PLANT GROWTH AND PROTECT PLANTS, BASED ON OXIME ETHERS AND OXIME ESTERS

This is a division of application Ser. No. 129,499 filed on Mar. 11, 1980, now U.S. Pat. No. 4,466,822; which is a division of application Ser. No. 881,953, filed on Feb. 27, 1978 now abandoned.

DETAILED DISCLOSURE

The present invention relates to novel oxime ethers and oxime esters of the general formula I

 (I)

to their production, and also to novel compositions based on these compounds, and to the application of these compositions or compounds for promoting plant growth or for protecting cultivated plants.

In the formula I

Ar represents a phenyl group of the formula

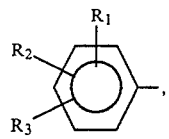

an α- or β-naphthyl group, or a heterocyclic ring of the formula

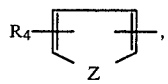

X represents —CN, —NO₂, halogen, lower alkanoyl, a carboxylic acid ester group, hydrogen, a carboxylic acid amide group, or lower alkyl, Q represents lower alkyl which is straight-chain or branched chain, or which can be interrupted by hetero atoms or substituted by halogen, or represents lower alkenyl or haloalkenyl, lower alkynyl, $C_3$—$C_7$-cycloalkyl optionally substituted by halogen, or represents lower cyanoalkyl, a lower alkanecarboxylic acid ester group, a lower alkanecarboxylic acid amide group, an aliphatic acyl group, an araliphatic, cycloaliphatic or optionally substituted aromatic or heterocyclic acyl group, alkylsulphonic acid or a sulphonic acid amide group, $R_1$ represents hydrogen, halogen, lower alkyl, lower alkoxy, or a phenoxy group which is in the para position and which is optionally substituted a maximum of twice by halogen, —CH, NO₂ or CF₃, $R_2$ and $R_3$ independently of one another represent hydrogen, halogen, NO₂, lower alkyl, halogenoalkyl or lower alkoxy, $R_4$ and $R_5$ independently of one another represent hydrogen, halogen, NO₂ or lower alkyl, and Z represents oxygen or sulphur, with the proviso that, if Ar represents an unsubstituted phenyl group and Q represents the radical —CH₂CN, X represents NO₂, halogen, lower alkanoyl, a carboxylic acid ester group, hydrogen, a carboxylic acid amide group, or lower alkyl.

Depending on substitution of these oxime derivatives of the general formula I, there are obtained products which have various properties influencing plant growth, and which can be used, in agriculture generally or in special areas of plant protection, as plant-growth regulators or alternatively as antidotes (safeners) for pesticides.

By halogen in the formula I is meant fluorine, chlorine, bromine or iodine.

The expression alkyl on its own or as part of a substituent embraces branched-chain or straight-chain $C_1$- to $C_8$-alkyl groups; and lower alkyl denotes $C_1$–$C_4$- alkyl. Examples are methyl, ethyl, propyl, isopropyl, butyl, isobutyl, sec-butyl or tert-butyl, as well as the higher homologues amyl, isoamyl, hexyl, heptyl or octyl, together with their isomers. Analogeously, alkanoyls or cyanoalkyls contain an additional C atom. A lower alkanecarboxylic acid ester consists of a lower alkyl part having 1–4 C atoms, the carbonyl group and an alcoholic or phenolic radical having 1 to 8 C atoms. To be mentioned in particular are acetic ester —CH₂—COOT (T=$C_1$-$C_8$-radical) and 1-propion ester —CH(CH₃)—COOT, with OT=a lower aliphatic alcohol radical being preferred in both cases.

Alkenyls denote aliphatic radicals having one or also two double bonds ("alkadienyls") and a maximum of 6, preferably 4, C atoms. Halogenalkenyls contain up to 3 halogen atoms, preferably chlorine or bromine. Lower alkynyl denotes propynyl (=propargyl) and butynyl.

Carboxylic acid amides and sulphonic acid amides embrace also monosubstituted or symmetrically or unsymmetrically disubstituted amides, with the substituents being optionally lower alkyl, lower alkenyl, propynyl or butynyl, and also once a phenyl ring, which can be substituted or unsubstituted according to the definition for $R_2/R_3$.

$C_3$–$C_7$-cycloalkyl groups are cyclopropyl, cyclobutyl, cyclopentyl, cyclohexyl and cycloheptyl, Cycloaliphatic radicals correspond to these ring systems, but they can also contain, depending on possibility, one or more double bonds.

An araliphatic radical includes an aryl group, such as phenyl, optionally mono- to trisubstituted according to $R_2/R_3$, or naphthyl, fluorenyl, or indanyl, which is bound by way of lower alkyl or lower alkenyl to the radical of the molecule. Examples are the fundamental substances benzyl, phenethyl, phenylallyl, as well as homologues.

Aromatic carboxylic acids, which can form the aromatic acyl groups, are derived from aromatic substances, such as in particular phenyl, and can be substituted as defined under $R_2/R_3$.

Heterocyclic carboxylic acids are derived from mono- or bicyclic rings having 1 to 3 identical or different hetero atoms O, S, and N. To be mentioned are 3- to 6-membered, especially 5- or 6-membered, heterocycles, which can be saturated, partially saturated or unsaturated, and can be optionally substituted as defined under $R_4/R_5$. Examples which may be mentioned but which do not constitute any limitation are: furan, nitrofuran, bromofuran, methylfuran, thiophene, chlorothiophene, pyridine, 2,6-dichlorpyridine, pyrimidine, pyridazine, pyrazine, piperidine, methylpiperidine, morpholine, thiomorpholine, tetrahydrofuran, oxazole, pyrazole, pyrrole, pyrroline, pyrrolidine, thiazole, 2,3-dihydro-4H-pyrane, pyrane, dioxane or 1,4-oxathi-(2)-ine.

Examples of aliphatic chains interrupted by hetero atoms are methoxyethyl, ethoxyethyl, propoxyethyl, butoxyethyl, methoxypropyl, ethylthioethyl, methylaminoethyl, tert-butylaminoethyl or alkoxyalkoxyalkyl, such as methoxyethoxyethyl.

It has been shown that oxime ethers and oxime esters of the formula I have for practical purposes extraordinarily advantageous properties for promoting plant growth, without there being any disadvantageous consequences for the plants treated therewith. Applied in small dosage amounts, active substances of the formula I have in particular the ability to stimulate both the genrminating seed and the young plants which are developing. With specific dosage amounts, this leads to a clearly enlarged root system, to an increased rate of photosynthesis and to a more rapid development of parts of plants above the soil. The action of the oximes of the formula I is however not restricted to the early stage of plant development, but can be observed also in the case of later application, or in the case of a partial application to specific parts of plants (seed dressings, pre-swelling of the seed, root treatment, treatment of shoots of leaf application). This manner of treatment leads to a more rapid growth of the treated plant, to improved fruit setting, to an earlier point of time of ripening and of harvesting and to an increased or otherwise improved crop yield. The active substances can be applied to the plant, to parts of the plant, to the seed or to the soil, and the mode of application corresponds to customary techniques of application or of dressing. A further very important advantage is the improvement in the power to compete of the plant treated in this manner compared with that of the weed flora which has not been growthstimulated. The active substance of the formula I must of course be applied in this case to the seed for to the seedlings of the desired crop of plants and not to the crop area in general. A third important advantage, which is a result of the greatly expanding root system of a plant thus treated, is the possibility, even under environmental conditions that are not particularly favourable, of achieving a satisfactory development of the crop of cultivated plants and thus an adequate crop yield. Examples which may be mentioned of such disturbance factors hostile to the environment are: soils low in nutrients, drought, low temperatures during the early development of the plant, sudden frosts, and reduced sunlight in consequence of an unfavourable time of the year or of an unfavourable location.

Oxime ethers and oxime esters of the formula I possess however to a very great extent properties for regulating plant growth, depending on the point of time of application and on the type of plant.

Various other possibilities of application of the oximes of the formula I may be listed as follows, but they do not constitute a limitation:
application for improved leaf formation in crops of tobacco, cabbage or lettuce, and avoidance of undesirable side shoots;
application for increasing yield in crops of leguminosae (e.g. in crops of peas, beans, soya beans and peanuts) by promoting generative growth (increase of tillering);
application for increasing the rigidity of crops prone to flattening, such as cereals (prevention of the sagging of plants under unfavourable weather conditions, such as storms or continual rain);
application for facilitating harvesting of fruit by promoting the formation of abscission layers between the fruit and the shoot part of the plant; and
application for raising the storage capacity for plant substances (sugar, proteins, oils, and so forth), or for temporarily maintaining that which has been stored.

The storage capacity for plant substances includes the possibility of retaining that already stored for longer than under natural conditions. Thus, the storability of potatoes can be improved. Furthermore, the sugar content in sugar cane shortly before harvesting can be kept constant by application of specific oxime ethers of the formula I, whereby the tendency of the plant to form further side shoots at the expense of the sugar content is counteracted.

Compositions for influencing plant growth, especially for inhibiting growth, have already been described at various times; thus, chlorocholine chloride in particular is suitable for the shortening and stabilising of the stems in wheat crops. According to German Offenlegungsschrift No. 2,458,165, bis(p-chlorophenyl)-acetic acid, or salts, esters amides or nitriles thereof, are said to effect a similar shortening of stems in cereal crops. In German Offenlegungsschrift No. 2,407,148, 2,6-disubstituted phenoxyacetates or 2,6-disubstituted phenoxypropionates are recommended as growth regulators. The mode of acting of these substances, particularly with low applied amounts and low concentrations, is however not satisfactory. The position is similar in the case of p-chlorophenyldimethylacetic acid (East German Patent Specification No. 113,890), and also in the case of 2-cyano-bicyclo[2,2,1]heptane (French Patent Specification No. 2,256,722). As was shown by tests, the action of these compounds is very unsatisfactory.

The arylglyoxilnitrile oximes, suggested in the U.S. Patent Specification No. 3,799,757, of the general formula

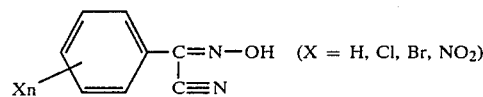

are insufficiently effective as growth inhibitors and plant-growth regulators; they are moreover not stable and decompose after a fairly short period of time.

Oximes of the formula I surprisingly possess a further very important property. They are excellently suitable for protecting cultivated plants, such as cultivated millet, rice, maize, varieties of cereals (wheat, rye, barley or oats), cotton, sugar beet, sugar cane, soya bean, etc., against being attacked by agricultural chemicals, particularly by herbicides of the widest variety of classes of substances, such as triazines, phenylurea derivatives, carbamates, thiolcarbamates, halogenoacetanilides, halogenophenoxyacetates, substituted phenoxyphenoxyacetates and -propionates, substituted pyridineoxyphenoxyacetates and -propionates, benzoic acid derivatives, etc., in cases where these do not act selectively or not sufficiently selectively, that is to say, damage to a greater or lesser extent the cultivated plants in addition to the weeds to be combated. The invention relates also to compositions which contain these oxime ethers of the formula I, together with biologically acting additives, such as herbicides, fungicides or insecticides.

Various substances have already been suggested for overcoming this problem, which substances are able to specifically antagonise the harmful action of a herbicide on the cultivated plant, i.e. to protect the cultivated plant without noticeably affecting the herbicidal action on the weeds to be combated. Depending on its properties, such an antidote can be used for the preliminary treatment of the seed of the cultivated plant (dressing of the seed or of the seedlings); or it can be applied into the seed furrows before sowing; or it can be applied as a tank mixture, on its own or together with the herbicide, before or after emergence of the plants. The treatment with the antidote can be carried out before or after, or simultaneously with, the herbicidal treatment. The pre-emergence treatment includes both the treatment of the cultivated area before sowing (ppi=pre plant incorporation) and the treatment of the sown cultivated area before emergence of the plants.

Thus, the British Patent Specification No. 1,277,557 describes the treatment of seed and seedlings of wheat and sorghum with certain esters and amides of oxamic acid before the attack by N-methoxymethyl-2',6'-diethyl-chloroacetanilide (Alachlor). Other publications (German Offenlegungsschriften Nos. 1,952,910 and 2,245,471, and French Patent Specification No. 2,021,611) suggest antidotes for the treatment of cereals, maize seed and rice seed to protect them against the attack from herbicidal thiolcarbamates. In German Patent Specification No. 1,576,676 and U.S. Patent Specification No. 3,131,509, hydroxyamino-acetanilides and hydantoins are suggested for protecting cereal seeds against carbamates, such as IPC, CIPC, etc.

However, there has not hitherto been suggested in the literature a class of substances which on the one hand are able to impart to plants strong growth-stimulating impulses, and on the other hand have the ability to protect, in the sense of an antidote effect, plants against aggressive agricultural chemicals.

Compounds of the formula I to be particularly emphasized are those wherein Ar has the given meaning, and the other substituents have the following meanings:
  X represents cyano, nitro, halogen, lower alkanoyl, a carboxylic acid ester group of a lower aliphatic alcohol, a carboxylic acid amide group, or lower alkyl,
  Q represents lower alkyl which is straight-chain or branched-chain, or which can be interrupted by a hetero atom or substituted by halogen, or Q represents lower alkenyl, lower alkynyl, lower cyanoalkyl, a lower alkanecarboxylic acid ester group, a lower alkanecarboxylic acid amide group, a lower aliphatic acyl group, a cycloaliphatic acyl group having 4 to 6 C atoms, or an unsubstituted sulphonic acid amide group or a sulphonic acid amide group mono- or disubstituted by a lower aliphatic radical,
  $R_1$ hydrogen, or a phenoxy group in para-position,
  $R_2$ and $R_3$ independently of one another represent hydrogen, halogen or lower alkyl,
  $R_4$ and $R_5$ represent hydrogen, and
  Z represents oxygen or sulphur.

Preferred compounds amongst these are compounds of the formula Ia

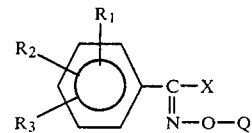

wherein the substituents have the following meanings:
  X represents cyano, nitro, halogen, lower alkanoyl, a carboxylic acid ester group of a lower aliphatic alcohol, a carboxylic acid amide group or lower alkyl,
  Q represents a lower straight-chain alkyl chain which is interrupted by oxygen, or Q represents lower alkenyl, lower alkynyl, lower cyanoalkyl, a lower alkanecarboxylic acid ester group, a lower alkanecarboxylic acid amide group, a lower aliphatic acyl group, a sulphonic acid amide group which is unsubstituted or is mono- or disubstituted by a lower aliphatic radical,
  $R_1$ represents hydrogen,
  $R_2$ represents hydrogen, halogen, lower alkyl or lower alkoxy, and
  $R_3$ represents hydrogen, halogen, lower alkyl or lower alkoxy.

Particularly preferred compounds of this last-mentioned group are those compounds wherein the substituents of the formula Ia have the following meanings:
  X represents cyano, nitro, halogen, lower alkanoyl, a carboxylic acid ester group of a lower alkanol, or a carboxylic acid amide group,
  Q represents lower alkynyl, lower cyanoalkyl, a lower alkanecarboxylic acid ester group, a lower alkanecarboxylic acid amide group,
  $R_1$ represents hydrogen,
  $R_2$ represents hydrogen, halogen or lower alkyl, and
  $R_3$ represents hydrogen, halogen or lower alkyl.

Preferred compounds within the last-mentioned group are, within narrower limits, those compounds wherein the substituents of the formula Ia have the following meanings:
  X represents cyano, chlorine, bromine, acetyl, propionyl, $-COOCH_3$, $-COOC_2H_5$, $-CO-NH_2$, $-CO-NHCH_3$ or $-CO-N(CH_3)_2$,
  Q represents propynyl or butynyl, cyanomethyl or cyanoethyl, methoxycarbonylmethyl, ethoxycarbonylmethyl, methoxycarbonylethyl or ethoxycarbonylethyl, an acetamide or propionamide group optionally substituted on the N atom by one or two lower aliphatic groups,
  $R_1$ represents hydrogen,
  $R_2$ represents hydrogen, halogen or methyl, and
  $R_3$ represents hydrogen, halogen or methyl.

Compounds amongst these which form an important subgroup are those wherein X represents a cyano group.

Another preferred range of active substances of the formula I which promote plant growth and protect plants is that embraced by the formula II

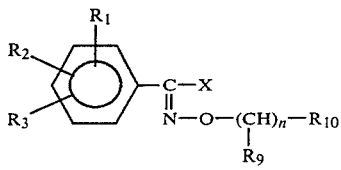 (II)

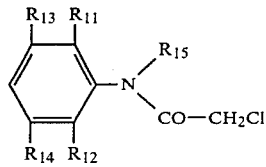 (IV)

wherein
R₁, R₂ and R₃ independently of one another represent hydrogen, halogen, NO₂, lower alkyl, halogenoalkyl or lower alkoxy,
X represents —CN, —NO₂, halogen, the acetyl group, a carboxylic acid ester group of a lower aliphatic alcohol or a carboxylic acid amide group,
n represents 1, 2 or 3,
R₉ represents hydrogen or lower alkyl,
R₁₀ represents —CONH₂, —CO—NH—lower aliphatic radical), —CO—NH—cycloalkyl, —CONH—(C₆H₅₋ₘ) (halogen, lower alkyl)ₘ or —CN, and
m represents an integer, 0, 1, 2 or 3.
Preferred compounds within the compass of the formula II are compounds of the formula III

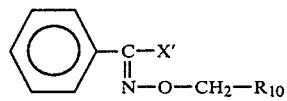 (III)

wherein
X' represents —CN, —NO₂, chorine, acetyl, lower alkoxycarbonyl, allyloxycarbon-, carbamoyl or di-lower-alkylcarbamoyl,
R₁₀ represents —CN, —CO—NH₂, —CO—NH—lower alkyl or —CONH(C₆H₅₋ₘ) (Cl, Br, CH₃)ₘ, and
m represents an integer, 0, 1 or 2.
The preferred individual compounds include:
α-cyanobenzylidene-amino-oxacetamide of the formula

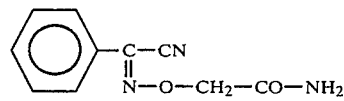

α-cyanobenzylidene-amino-oxyacetic acid ethyl ester (Comp. 1.4),
α-(cyanoethoximino)-benzacetonitrile (Comp. 1.44).

Effective chloroacetanilides, which in some cases are not sufficiently tolerated by cultivated plants, such as cereals, rice, cultivated sorghum, and so forth, but which, when acting together with the oxime ethers of the formula I of the present invention, leave such cultivated plants unharmed, without losing any of their normal effectiveness against weeds, have become known, for example, from the U.S. Pat. Nos. 3,547,620, 3,403,994, 3,442,945, 3,637,847, 3,598,859, 3,819,661, 3,946,045 and 3,983,174, and from the German Offenlegungsschriften Nos. 2,212,268, 2,305,495, 2,328,340, 2,402,983, 2,405,183 and 2,405,479.

The antidotes of the formula I, II or III are used preferably together with herbicidal chloroacetanilides of the formula wherein
R₁₁ represents lower alkyl, alkoxy, alkoxyalkyl, trifluoromethyl or halogen,
R₁₂, R₁₃ and R₁₄ independently of one another represent hydrogen, lower alkyl, alkoxy, alkoxyalkyl, trifluoromethyl or halogen, and
R₁₅ represents a C₁–C₄-alkyl which is optionally substituted by carboxy, carboxylic acid ester, carbonamide, or carbonamide substituted by one or two lower aliphatic radicals, or by —CN; or wherein R₁₅ represents propynyl, butynyl, an acetalised carbonyl group, 1,3-dioxolan-2-yl-alkyl, 1,3-dioxolan-5-yl-alkyl, 1,3-dioxan-2-yl-alkyl, furanylmethyl, tetrahydrofuranylmethyl, or alkoxyalkyl of the form —A—O—R₁₆, wherein A represents an alkylene chain having 1 to 4 C atoms, of which 1 or 2 belong to the direct chain, and R₁₆ represents lower alkyl, alkenyl, or cycloalkyl or cycloalkylmethyl having 3 to 6 C atoms in the ring.

The expressions "lower alkyl" or "lower aliphatic radical" denote groups having at most 4 carbon atoms, and correspond to the aforementioned definition for the formula I, and likewise the term "halogen".

Some chloroacetanilides which are particularly suitable for use with the antidotes according to the invention are listed below:
N-ethoxymethyl-2-methyl-6-ethyl-chloroacetanilide,
N-methoxymethyl-2,6-diethyl-chloroacetanilide,
N-(2'-methoxyethyl)-2,6-dimethyl-chloroacetanilide,
N-(2'-allyloxyethyl)-2,6-dimethyl-chloroacetanilide,
N-(2'-n-propoxyethyl)-2,6-dimethyl-chloroacetanilide,
N-(2'-isopropoxyethyl)-2,6-dimethyl-chloroacetanilide,
N-(2'-methoxyethyl)-2-methyl-6-ethyl-chloroacetanilide,
N-(2'-methoxyethyl)-2,6-diethyl-chloroacetanilide,
N-(2'-ethoxyethyl)-2-methyl-6-ethyl-chloroacetanilide,
N-[3'-methoxyprop-(2')-yl]-2-methyl-chloroacetanilide,
N-[3'-methoxyprop-(2')-yl]-2,6-dimethyl-chloroacetanilide,
N-[3'-methoxyprop-(2')-yl]-2-methyl-6-ethyl-chloroacetanilide,
N-[3'-methoxyprop-(2')-yl]-2,6-diethyl-chloroacetanilide,
N-(2'-ethoxyethyl)-2,6-diethyl-chloroacetanilide,
N-(2'-n-propoxyethyl)-2-methyl-6-ethyl-chloroacetanilide,
N-(2'-n-propoxyethyl)-2,6-diethyl-chloroacetanilide,
N-(2'-isopropoxyethyl)-2-methyl-6-ethyl-chloroacetanilide,
N-chloroacetyl-2,6-dimethylanilino-acetic acid ethyl ester,
N-chloroacetyl-2,6-diethylanilino-acetic acid ethyl ester,
N-chloroacetyl-2,6-dimethylanilino-acetic acid methyl ester,
N-chloroacetyl-2-methyl-6-ethylanilino-acetic acid isopropyl ester,
2-[N-(α-chloroacetyl)-2,6-dimethylanilino]acetaldehyde-diethylacetal, N-[3'-methoxyprop-(2')-yl]-2,3-dimethyl-chloroacetanilide,
N-(2'-ethoxyethyl)-2-methyl-chloroacetanilide,
N-(2'-methoxyethyl)-2-methyl-chloroacetanilide,
N-[2'-methoxyprop-(1')-yl]-2,6-dimethyl-chloroacetanilide,
N-[2'-methoxyprop-(1')-yl]-2-methyl-6-ethyl-chloroacetanilide,
N-[3'-ethoxyprop-(2')-yl]-2-methyl-6-ethyl-chloroacetanilide,
N-[1'-methoxybut-(2')-yl]-2,6-dimethyl-chloroacetanilide,
N-(2'-methoxyethyl)-2-methyl-6-methoxy-chloroacetanilide,
N-(n-butoxymethyl)-2-tert.butyl-chloroacetanilide,
N-[3'-ethoxyprop-(2')-yl]-2,6-dimethyl-chloroacetanilide,
N-(2'-methoxyethyl)-2-chloro-6-methyl-chloroacetanilide,
N-(2'-ethoxyethyl)-2-chloro-6-methyl-chloroacetanilide,
N-(2'-ethoxyethyl)-2,3,6-trimethyl-chloroacetanilide,
N-(2'-methoxyethyl)-2,3,6-trimethyl-chloroacetanilide,
N-(2'-isopropoxyethyl)-2,3,6-trimethyl-chloroacetanilide,
N-cyanomethyl-2,6-dimethyl-chloroacetanilide,
N-(but-1-in-3-yl)-chloroacetanilide,
N-propynyl-2-methyl-6-ethyl-chloroacetanilide,
N-(1,3-dioxolan-2-ylmethyl)-2,6-dimethyl-chloroacetanilide,
N-(1,3-dioxolan-2-ylmethyl)-2-ethyl-6-methyl-chloroacetanilide,
N-(1,3-dioxan-2-ylmethyl)-2-methyl-6-ethyl-chloroacetanilide,
N-(2'-furanyl-methyl)-2,6-dimethyl-chloroacetanilide,
N-(2'-furanyl-methyl)-2-chloro-6-methyl-chloroacetanilide,
N-(2'-tetrahydrofuranyl-methyl)-2,6-dimethyl-chloroacetanilide,
N-(N'-propargylcarbamylmethyl)-2,6-dimethyl-chloroacetanilide,
N-(N',N'-dimethylcarbamylmethyl)-2,6-dimethyl-chloroacetanilide,
N-(n-butoxymethyl)-2,6-diethyl-chloroacetanilide,
N-(2'-butoxyethyl)-2,6-diethyl-chloroacetanilide,
N-[3'-methoxybut-(2')-yl]-2,6-dimethyl-chloroacetanilide, and
2-chloro-N-isopropylacetanilide.

Suitable herbicidal thiocarbamates which when used, in crops of cereals, rice or cultivated sorghum, together with compounds of the formula I, II or III are made more compatible with the crops correspond preferably to the formula

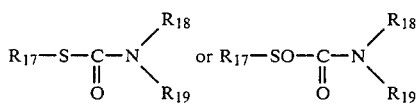

wherein
R$_{17}$ represents lower alkyl, alkenyl, chloroallyl, dichloroallyl, trichloroallyl, benzyl or p-chlorobenzyl,
R$_{18}$ represents C$_2$-C$_4$-alkyl, and
R$_{19}$ represents C$_2$-C$_4$-alkyl or cyclohexyl, or wherein R$_{18}$ and R$_{19}$ together with the N atom form a hexahydro-1H-azepine ring, a decahydroquinoline ring or a 2-methyl-decahydroquinoline ring.

The following thiolcarbamates may be mentioned as examples of such compounds:
S-ethyl-N,N-dipropylthiocarbamate,
S-ethyl-N,N-diisobutylthiocarbamate,
S-2,3-dichloroallyl-N,N-diisopropylthiolcarbamate,
S-propyl-N-butyl-N-ethylthiolcarbamate,
S-2,3,3-trichloroallyl-N,N-diisopropylthiolcarbamate,
S-propyl-N,N-dipropylthiolcarbamate,
S-ethyl-N-ethyl-N-cyclohexylthiolcarbamate,
S-ethyl-N-hexahydro-1H-azepine-1-carbothioate,
S-isopropyl-N,N-hexamethylene-thiolcarbamate,
S-(p-chlorobenzyl)-N,N-diethylthiolcarbamate,
N-ethylthiocarbonyl-cis-decahydroquinoline,
N-propylthiocarbonyl-decahydroquinaldine,
S-ethyl-N,N-bis-(n-butyl)-thiolcarbamate, and S-tert.butyl-N,N-bis-(n-propyl)-thiolcarbamate.

Further examples of thiolcarbamates that can be used are described in the U.S. Pat. Nos. 2,913,327, 3,037,853, 3,175,897, 3,185,720, 3,198,786 and 3,582,314.

The following may be mentioned as further preparations which with compounds of the formula I can be made more compatible with the crops of cultivated plants:
α-[4-(2,4-dichlorophenoxy)-phenoxy]-propionic acid methyl ester,
α-[4-(4-trifluoromethylphenoxy)-phenoxy]-propionic acid methyl ester,
α-[4-(2-chloro-4-trifluoromethylphenoxy)-phenoxy]-propionic acid methyl ester, and
α-[4-(3,5-dichloropyridyl-2-oxy)-phenoxy]-propionic acid methyl ester.

The applied amount of antidote varies between about 0.01 and about 15 parts by weight per part by weight of herbicide. Which ratio with regard to the optimum effect on the specific cultivated plant is most suitable is determined from case to case, i.e. depending on the type of herbicide used.

As already mentioned, various methods and techniques are suitable for the application of the novel antidotes of the formulae I-III for protecting cultivated plants against agricultural chemicals, or for stimulating plant growth.

1. Seed dressing
a. Dressing of the seed with an active substance formulated as a wettable powder by shaking in a vessel until there exists a uniform distribution over the surface of the seeds (dry dressing). The amount of active substance of the formula I used for this purpose is about 10 to 500 g (40 g to 2 kg of wettable powder) per 100 kg of seed.

b. Dressing of the seed with an emulsion concentrate of the active substance of the formula I using method (a) (wet dressing).

c. Dressing by immersion of the seed in a liquor containing 50–3200 ppm of active substance of the formula I for 1–72 hours and, optionally, subsequent drying of the seed (immersion dressing).

The dressing of the seed or the treatment of the germinated seedlings are naturally the preferred methods of application because the treatment with the active substance is directed completely at the target crop. There is used as a rule 10 g to 500 g, preferably 50 to 250 g, of active substance per 100 kg of seed, with it being possible, depending on the method used, which enables also the addition of other active substances or micronutrients to be made, to deviate either upwards or downwards from the given limiting concentrations (repeat dressings).

2. Application as a tank mixture

A liquid preparation of a mixture of antidote and herbicide (reciprocal quantitative ratio between 10:1 and 1:10) is used, the applied amount of herbicide being 0.1 to 10 kg per hectare. A tank mixture of this kind is preferably applied before or immediately after sowing, or it is worked into the unsown soil to a depth of 5–10 cm.

3. Application into the seed furrow

The antidote is introduced, as an emulsion concentrate, wettable powder or granulate, into the open sown seed furrow and, after the covering of the seed furrow in the normal manner, the herbicide is applied using the pre-emergence process.

Essentially, the antidote can therefore be applied before, together with, or after the pesticide, and its application to the seeds or to the field can be effected either before or after sowing, or in certain cases also after germination of the seed. The invention relates in particular also to compositions which contain, besides the antidote of the formula I, at least one agrochemical active substance, e.g. a herbicide from the chloroacetanilide class or from the thiolcarbamate class. These compositions contain in addition also carrier substances and/or distributing agents.

4. Controlled release of active substance

The active substance in solution is absorbed onto mineral granulate carriers or onto polymerised granulates (urea/formaldehyde), and the material is allowed to dry. It is possible if desired to apply a coating (coated granules), which enables the active substance to be released in controlled amounts over a specific period of time.

It is naturally possible to use also all other known methods of applying active substances. Examples in this respect are given further on in the text.

The process according to the invention for promoting plant growth or for protecting cultivated plants can be applied in particular to rice and to cultivated millet of the sorghum variety, also to maize, wheat, barley, oats, soya bean, cotton and sugar beet. It is however not limited to the promotion and protection of annual plants, but is also very suitable for growth stimulation of perennial plants (fruit trees, ornamental shrubs, and so forth), where it is desired to promote root formation or the formation of side shoots, or to achieve improved fruit setting or improved inflorescence.

The compounds of the formula I are produced by processes known per se (Organic Reactions 1953, Vol. 7, pages 343 and 373; Journal f. prakt. Chemie 66, page 353; Liebigs Ann. 250, 165.), namely by etherification or acylation of an oxime of the formula V

or of its oxime salt, with a halide of the formula Halg-Q, wherein Ar, X and Q have the meanings given for the formula I, and "Halg" denotes halogen, preferably chlorine or bromine.

The condensation of substituted α-ozimino compounds is effected in the case of etherification advantageously with the compounds in the form of their salts, particularly in the form of their alkali metal salts or ammonium salts, as is shown in the following by selected examples:

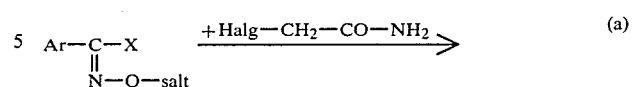

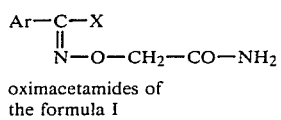

oximacetamides of the formula I

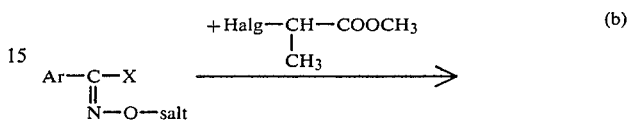

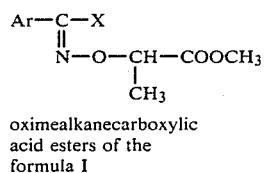

oximealkanecarboxylic acid esters of the formula I

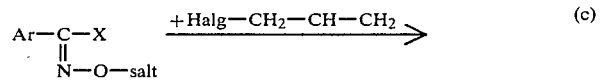

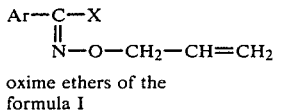

oxime ethers of the formula I

Acylation is effected advantageously with the free oximes of the formula V, as is shown by the following diagrams:

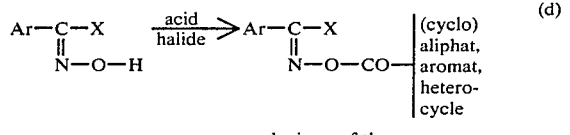

acyloximes of the formula I

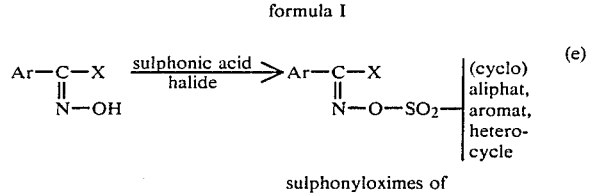

sulphonyloximes of the formula I (In the above diagrams, "Halg" denotes halogen, especially Cl or Br)

Suitable as solvents for obtaining the compounds of the formula I are essentially all representatives which behave inertly under the conditions of the reaction. For example, hydrocarbons, particularly however polar solvents, such as acetonitrile, dioxane, cellosolve or DMF, but also ketones, such as methyl ethyl ketone, acetone, etc. Solvents containing hydroxyl groups are excluded.

The temperatures are in the range of −10° C. to about 150° C., preferably between 20° and 120° C.

As agents splitting off hydrogen halide, it is possible to use bases such as tert. amines (triethylamine, triethylenediamine, piperidine, etc.). Also a suspension of sodium carbonate in the anhydrous reaction medium suffices in some cases.

Oximes are present in two stereoisomeric forms, the syn-form and anti-form. Also the compounds of the formula I mentioned under (a) to (e) can be present in either of these forms in the pure state or as mixtures of both. By 'compounds of the formula I' are accordingly meant, within the scope of the present specification, both stereoisomeric forms on their own, or as mixtures with each other in any reciprocal quantitative ratio.

The following Examples illustrate the production of the novel oximes of the formula I.

EXAMPLE 1

17 g (0.1 mol) of phenylglyoxylonitrile-2-oxime sodium salt is suspended in 170 ml of acetonitrile in a 350 ml sulphonating flask. There is then added 23.8 g (0.1 mol) of chloroaceto-3,4-dichloroanilide, whereupon a slight reaction heating can be detected. The suspension is refluxed for 3 hours, with the suspension changing in appearance. After cooling to room temperature, the formed sodium chloride is filtered off; the residue is subsequently washed with acetonitrile, and the combined filtrates are then concentrated in vacuo to leave as residue 32.3 g of crude product. Recrystallisation from alcohol/water yields 20.4 g of final product of the formula

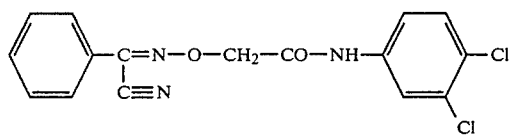

m.p. 143°–144° C.

From the salt of 2,4-dimethylphenylhydroxamic acid chloride and allyl chloride, there is correspondingly obtained as an oily substance the product of the formula

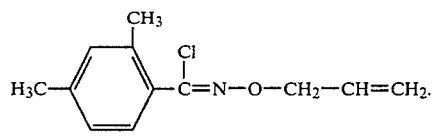

In a similar manner is obtained from 2-thienylacetonitrileoxime sodium salt and chloroacetonitrile the compound

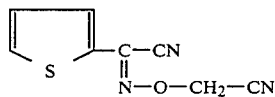

as oil substance.

EXAMPLE 2

33.6 g (0.2 mol) of phenylglyoxylonitrile-oxime sodium salt and 25 g (0.22 mol) of chloroacetic acid methyl ester in 200 ml of acetonitrile are held for 3 hours at 60°–70° C. with thorough stirring, in which time the suspension becomes greatly refined. After a further few hours, filtration is performed; the residue is subsequently washed with acetonitrile, and the combined filtrates are concentrated in vacuo to leave an oily residue, which becomes solid after about 24 hours, m.p. 68°–70° C.; Recrystallised from isopropanol: m.p. 71°–72° C.

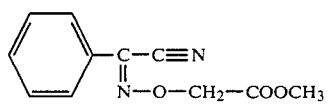

In a similar manner is obtained, by condensation of 4-chlorophenylglyoxylonitrile-oxime sodium salt with α-chloropropionic acid ethyl ester, the compound of the formula

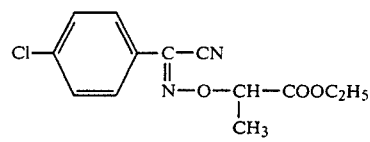

in 99.3% yield in the form of oil.

If there is used, instead of the α-chloropropionic acid ester, the chloroacetic acid isopropyl ester, there is obtained the compound of the formula

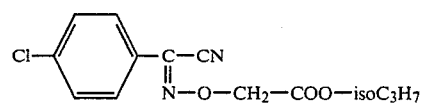

m.p. 93°–94° C.; and with use of the unsubstituted phenylglyoxylonitrile oxime (as Na salt) there is obtained the compound of the formula

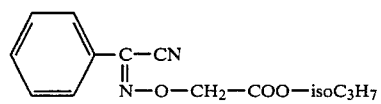

m.p. 49°–50° C.

EXAMPLE 3

Production of

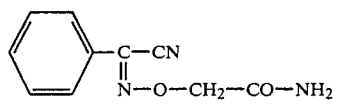

α-Cyanobenzylidene-amino-oxacetamide 845 g (5 mols) of benz-acetonitrileoxime as Na salt is suspended in 2.5 liters of acetonitrile, and there is slowly added in the presence of catalytic amounts of KJ, with stirring, 468 g (5 mols) of chloroacetamide. The reaction mixture is refluxed for 12 hours; it is then cooled and subsequently allowed to flow into about 12 liters of water. While the salts present are dissolving, the final product precipitates in crystalline form: 882 g (=86.8% of theory), m.p. 128°–129° C. (from ethanol).

There is correspondingly obtained, from the sodium salt of 3-furanylnitromethane-oxime and methanesulphonyl chloride, the compound of the formula

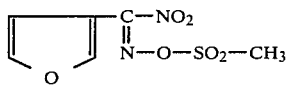

in the form of viscous oil.

EXAMPLE 4

8.0 g (0.037 mol) of the sodium salt of α-oximino-1-naphthylacetonitrile and 5.5 g (0.045 mol) of propargyl bromide in 50 ml of acetonitrile are heated for 4 hours at about 80° C. The suspension is afterwards concentrated in vacuo, and the residue is extracted with methylene chloride. The solution is concentrated by evaporation to leave the compound of the formula

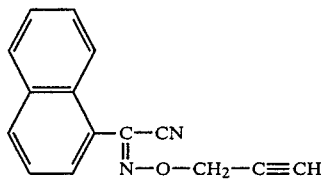

as oil.

Analysis for $C_{15}H_{10}N_2O$ calculated: C 76.9% H 4.3% N 11.96% found: C 76.4% H 4.4% N 11.8%.

If there is used as reactant, instead of propargyl bromide, chloroacetonitrile, there is obtained the compound of the formula

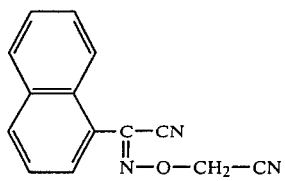

m.p. 81°–82° C.

EXAMPLE 5

0.1 mol of the sodium salt of α-oximino-2-thienylacetonitrile with 0.12 mol of chloroacetamide is suspended in 150 ml of acetonitrile. The suspension is heated for 3 hours at 50°–60° C., with NaCl precipitating; this is filtered off and washed with acetonitrile. The filtrates are concentrated in vacuo to yield the compound of the formula

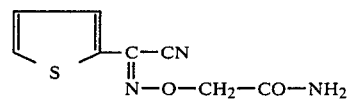

as a light-yellow oily substance.

The temperatures are given in degrees Centigrade in the following Tables.

The following compounds can be produced by the methods described above:

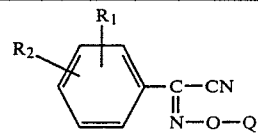

| Comp. No. | $R_1$ | $R_2$ | Q | |
|---|---|---|---|---|
| 1.1 | H | H | —CH$_2$—CO—NH$_2$ | m.p. 128–129° |
| 1.2 | 4-Cl | H | —CH$_2$—CO—NH$_2$ | m.p. 126–128° |
| 1.3 | H | H | —CH$_2$—COOCH$_3$ | m.p. 71–72° |
| 1.4 | H | H | —CH$_2$—COOC$_2$H$_5$ | m.p. 54–56° |
| 1.5 | H | H | —CH$_2$—COO(i-C$_3$H$_7$) | m.p. 49–50° |
| 1.6 | 4-CH$_3$ | H | —CH(CH$_3$)COOCH$_3$ | oil |
| 1.7 | 4-Cl | H | —CH$_2$—COO(i-C$_3$H$_7$) | m.p. 93–94° |
| 1.8 | 4-Cl | 2-Cl | —CH$_2$—COOCH$_3$ | oil |
| 1.9 | 4-Cl | 2-Cl | —CH$_2$—COOC$_2$H$_5$ | oil |
| 1.10 | 4-Cl | 3-Cl | —CH$_2$—COOCH$_3$ | oil |
| 1.11 | 4-Cl | 3-Cl | —CH$_2$—COOC$_2$H$_5$ | oil |
| 1.12 | 4-Cl | H | —CH(CH$_3$)—COOC$_2$H$_5$ | oil |
| 1.13 | 4-CH$_3$O— | H | —CH$_2$—COOC$_2$H$_5$ | m.p. 78–81° |
| 1.14 | H | H | —CH$_2$—C≡CH | oil |
| 1.15 | H | 2-Cl | —C$_2$H$_5$ | oil |
| 1.16 | 4-CH$_3$ | H | —nC$_3$H$_7$ | oil |
| 1.17 | 4-CH$_3$O | H | —CH$_3$ | m.p. 75–77° |
| 1.18 | 4-CH$_3$O | H | —C$_2$H$_5$ | oil |
| 1.19 | 4-Br | H | —CH$_2$—C≡CH | m.p. 90–92° |
| 1.20 | H | H | —CH$_2$—CH—CH$_2$ with Cl, Cl | b.p. 118–120°/10.5 Torr |
| 1.21 | 4-Cl | H | —CH(C$_2$H$_5$)—COOC$_2$H$_5$ | oil |
| 1.22 | 4-Cl | H | —CH$_2$—C≡CH | semisolid |
| 1.23 | 4-Cl | H | —CH(CH$_3$)—COOCH$_3$ | oil |
| 1.24 | 4-CH$_3$ | H | —C$_2$H$_5$ | oil |
| 1.25 | 4-Cl | 2-Cl | —CH(CH$_3$)—C≡CH | oil |
| 1.26 | 4-Br | H | —CH$_3$ | m.p. 60–62° |
| 1.27 | 3-CF$_3$ | H | —CH$_2$—COOC$_2$H$_5$ | |
| 1.28 | 3-CF$_3$ | H | —CH$_2$HC=CH$_2$ | |

-continued

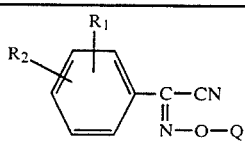

| Comp. No. | R₁ | R₂ | Q | |
|---|---|---|---|---|
| 1.29 | H | H | —nC₄H₉ | |
| 1.30 | H | H | —CH₂—COO(isoC₄H₉) | |
| 1.31 | 3-CF₃ | H | —CH(CH₃)—COOC₂H₅ | |
| 1.32 | 4-NO₂ | H | —CH₂—COOCH₃ | |
| 1.33 | 4-NO₂ | H | —CH₂—CO—NH₂ | |
| 1.34 | H | H | —CH₂—CO—NH—(3,4-dichlorophenyl) | m.p. 143–144° |
| 1.35 | H | H | —SO₂N(CH₃)₂ | m.p. 88–89° |
| 1.36 | 4-Br | H | —CH₂—CN | m.p. 77–79° |
| 1.37 | 4-CH₃O | H | —C₂H₅ | solid |
| 1.38 | H | H | —CH₃ | m.p. 129–131° |
| 1.39 | H | H | —C₂H₅ | oil |
| 1.40 | H | H | —C₃H₇(iso) | oil |
| 1.41 | H | H | —CH(CH₃)COOCH₃ | oil |
| 1.42 | H | H | —CH(CH₃)COOC₂H₅ | m.p. 36–37° |
| 1.43 | H | H | —CH(C₂H₅)COOC₂H₅ | solid |
| 1.44 | H | H | —CH₂—CH₂—CN | m.p. 123–126° |
| 1.45 | H | H | —CH₂—CH₂—CH₂—CN | oil |
| 1.46 | H | H | —CO—CH₃ | m.p. 68–70° |
| 1.47 | 3-CF₃ | H | —CH₂—COOCH₃ | m.p. 107–109° |
| 1.48 | 2-CH₃ | H | —CH₂—CN | |
| 1.49 | 2-F | H | —CH₂—CN | |
| 1.50 | 2-F | H | —CH₂—CONH₂ | oil |
| 1.51 | 2-CH₃ | H | —CH(CH₃)—COOCH₃ | |
| 1.52 | 4-Cl | H | —CH₂—CO—NH—(3,4-dichlorophenyl) | m.p. 158–160° |
| 1.53 | H | H | —CO—(2,5-dichloro-3-methoxyphenyl) | m.p. 97–99° |
| 1.54 | H | H | —(CH₂)₇—CH₃ | m.p. 131–133° |
| 1.55 | 4-nC₄H₉O | H | —CH₂—CN | |
| 1.56 | 4-isoC₃H₇O | H | —CH₂—CO—NH₂ | |
| 1.57 | 2-CH₃ | H | —CH₂—CO—NH₂ | oil |
| 1.58 | 3-NO₂ | H | —CH₂—CO—NH₂ | |
| 1.59 | 3-NO₂ | H | —SO₂—CH₃ | m.p. 133–135° |
| 1.60 | H | H | —CH₂—CO—CH₃ | m.p. 67–68° |
| 1.61 | H | H | —CH(CH₃)—CO—NH₂ | m.p. 144–146° |
| 1.62 | H | H | —SO₂—CH₃ | m.p. 121–122° |
| 1.63 | H | H | —CH₂—COOC₄H₉(tert.) | m.p. 76–77° |
| 1.64 | H | H | —CH(nC₁₀H₂₁)COOC₂H₅ | m.p. 53–54° |
| 1.65 | H | H | —C(CH₃)₂—COOC₂H₅ | oil |
| 1.66 | H | H | —CH(CH₃)—COOC₃H₇(iso) | oil |
| 1.67 | H | H | —(CH₂)₁₇—CH₃ | solid |
| 1.68 | H | H | —CH(CH₃)—C≡CH | oil |
| 1.69 | H | H | —CH(CH₃)—CON(C₂H₅)₂ | oil |
| 1.70 | H | H | —CH₂—CO—NH—CH₃ | |
| 1.71 | H | H | —CH₂—CO—N(CH₃)₂ | |
| 1.72 | H | H | —CH₂—CONH—CH₂—CH=CH₂ | |
| 1.73 | H | H | —CH₂—CONH—C≡CH | |
| 1.74 | H | H | —CH₂—CON(CH₃)—CH₂—CH=CH₂ | |
| 1.75 | H | H | —CH₂—CON(CH₃)—C₂H₅ | |
| 1.76 | H | H | —CH(CH₃)—CONH—CH₃ | |
| 1.77 | H | H | —CH(CH₃)—CON(CH₃)₂ | |
| 1.78 | H | H | —CH₂—CON(allyl)₂ | solid |

-continued

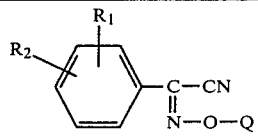

| Comp. No. | R₁ | R₂ | Q | |
|---|---|---|---|---|
| 1.79 | H | H | —C₆H₃(NO₂)₂(2,4) | m.p. 178–179° |
| 1.80 | H | H | —CH₂—C₆H₃Cl₂(3,4) | m.p. 91–93° |
| 1.81 | H | H | —CH₂—COOCH₂—C₆H₅ | m.p. 61–62° |
| 1.82 | H | H | —CH₂—COO—C₆H₄NO₂(4) | solid |
| 1.83 | H | H | —CH₂—CONH—C₆H₃Cl₂(3,5) | m.p. 149–150° |
| 1.84 | H | H | —CH₂—CONH—C₆H₄F(4) | m.p. 136–137° |
| 1.85 | H | H | —CO—C₂H₅ | m.p. 53–55° |
| 1.86 | H | H | —CH(CH₃)CN | m.p. 60–62° |
| 1.87 | H | H | —CH₂—CH=CH—CH₃ | oil |
| 1.88 | 4-CH₃ | H | —CH₂—CN | m.p. 82–84° |
| 1.89 | 4-CH₃ | H | —CH₃ | m.p. 44–46° |
| 1.90 | 4-CH₃ | H | —CH₂—COOCH₃ | solid |
| 1.91 | 4-CH₃ | H | —CH₂—COOC₂H₅ | solid |
| 1.92 | 4-CH₃ | H | —CH(CH₃)COOC₂H₅ | oil |
| 1.93 | 4-CH₃ | H | —CH(C₂H₅)COOC₂H₅ | oil |
| 1.94 | 4-CH₃ | H | —CH₂—CONH—C₆H₃Cl₂(3,4) | m.p. 162–164° |
| 1.95 | 4-CH₃ | H | —CH(CH₃)—COOC₃H₇(iso) | oil |
| 1.96 | 4-CH₃ | H | —CH₂C≡CH | solid |
| 1.97 | 4-CH₃ | H | —CH₂—CH=CH—CH₃ | oil |
| 1.98 | 4-CH₃ | 3-CH₃ | —CH₂—CN | m.p. 40° |
| 1.99 | 4-CH₃ | 3-CH₃ | —CH₃ | oil |
| 1.100 | 4-CH₃ | 3-CH₃ | —C₂H₅ | oil |
| 1.101 | 4-CH₃ | 3-CH₃ | —C₃H₇(n) | oil |
| 1.102 | 4-CH₃ | 3-CH₃ | —CH₂—COOCH₃ | m.p. ca. 60° |
| 1.103 | 4-CH₃ | 3-CH₃ | —CH₂—COOC₂H₅ | m.p. ca. 50° |
| 1.104 | 4-CH₃ | 3-CH₃ | —CH(CH₃)COOCH₃ | oil |
| 1.105 | 4-CH₃ | 3-CH₃ | —CH(CH₃)COOC₂H₅ | oil |
| 1.106 | 4-CH₃ | 3-CH₃ | —CH₂—C≡CH | m.p. 75–81° |
| 1.107 | 4-CH₃ | 3-CH₃ | —CH₂—CONH—C₆H₃Cl₂(3,4) | m.p. 110° |
| 1.108 | 4-CH₃ | 3-CH₃ | —CH₂—CONH—CH₃ | oil |
| 1.109 | 4-CH₃ | 3-CH₃ | —CH₂—CON(CH₃)CH₂—CH=CH₂ | oil |
| 1.110 | 4-CH₃ | 3-CH₃ | —CH₂—CONH₂ | oil |
| 1.111 | 4-OCH₃ | H | —CH₂—CN | m.p. 91–93° |
| 1.112 | 4-OCH₃ | H | —C₃H₇(n) | oil |
| 1.113 | 4-OCH₃ | H | —CH₂—COOCH₃ | m.p. 122–125° |
| 1.114 | 4-OCH₃ | H | —CH(CH₃)COOC₂H₅ | m.p. 50–53° |
| 1.115 | 4-OCH₃ | H | —CH(CH₃)COOCH₃ | oil |
| 1.116 | 4-OCH₃ | H | —CH(C₂H₅)COOC₂H₅ | oil |
| 1.117 | 4-OCH₃ | H | —CH(CH₃)C≡CH | solid |
| 1.118 | 4-OCH₃ | H | —CH₂—COOC₃H₇(iso) | solid |
| 1.119 | 4-OCH₃ | H | —CH(CH₃)COOC₃H₇(iso) | oil |
| 1.120 | 4-OCH₃ | H | —(CH₂)₇—CH₃ | oil |
| 1.121 | 4-OCH₃ | H | —CH₂—CO—NH₂ | m.p. 123–126° |
| 1.122 | 4-OCH₃ | H | —CH₂—C≡CH | solid |
| 1.123 | 4-OCH₃ | H | —CH₂—CH=CH₂ | m.p. ca. 40° |
| 1.124 | 4-OCH₃ | H | —CO—C₆H₅ | m.p. 128–130° |
| 1.125 | 4-OCH₃ | H | —CH₂—CH=CH—CH₃ | solid |
| 1.126 | 4-Cl | H | —CH₂—CN | m.p. 69–71° |
| 1.127 | 4-Cl | H | —CH₃ | m.p. 70–71° |
| 1.128 | 4-Cl | H | —C₂H₅ | m.p. 39–40° |
| 1.129 | 4-Cl | H | —C₃H₇(n) | oil |
| 1.130 | 4-Cl | H | —CH₂—COOCH₃ | m.p. 81–82° |
| 1.131 | 4-Cl | H | —CH₂—COOC₂H₅ | m.p. 79–80° |
| 1.132 | 4-Cl | H | —CH(CH₃)COOC₃H₇(iso) | oil |
| 1.133 | 4-Cl | H | —(CH₂)₇—CH₃ | oil |
| 1.134 | 4-Cl | H | —CH₂—CH=CH₂ | solid |
| 1.135 | 4-Cl | H | —CH₂—CONH—C₆H₃Cl₂(3,4) | m.p. 165–166° |
| 1.136 | 4-Cl | H | —CH₂—CONH—C₆H₄Br(4) | m.p. 199–201° |
| 1.137 | 4-Cl | H | —CH₂—CONH—C₆H₄CF₃(3) | m.p. 187–190° |
| 1.138 | 4-Cl | H | —CH₂—CONH—C₆H₄Cl(4) | m.p. 204–205° |
| 1.139 | 2-Cl | H | —CH₂—CN | m.p. 51–53° |
| 1.140 | 2-Cl | H | —CH₃ | oil |
| 1.141 | 2-Cl | H | —C₃H₇(n) | oil |
| 1.142 | 4-Cl | 2-Cl | —CH₂—CN | m.p. 126–128° |
| 1.143 | 4-Cl | 2-Cl | —CH₃ | m.p. 95–96° |
| 1.144 | 4-Cl | 2-Cl | —C₂H₅ | solid |
| 1.145 | 4-Cl | 2-Cl | —CH(CH₃)COOCH₃ | oil |
| 1.146 | 4-Cl | 2-Cl | —CH(CH₃)COOC₂H₅ | oil |
| 1.147 | 4-Cl | 2-Cl | —CH(C₂H₅)COOC₂H₅ | oil |
| 1.148 | 4-Cl | 2-Cl | —CH₂—C≡CH | solid |
| 1.149 | 4-Cl | 2-Cl | —CH₂—CH=CH—CH₃ | oil |
| 1.150 | 4-Cl | 3-Cl | —CH₃ | m.p. 84–85° |
| 1.151 | 4-Cl | 3-Cl | —C₂H₅ | solid |

-continued

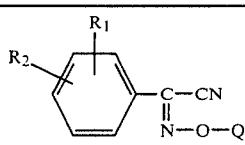

| Comp. No. | R₁ | R₂ | Q | |
|---|---|---|---|---|
| 1.152 | 4-Cl | 3-Cl | —C$_3$H$_7$(n) | oil |
| 1.153 | 4-Cl | 3-Cl | —C$_4$H$_9$(tert.) | solid |
| 1.154 | 4-Cl | 3-Cl | —CH(CH$_3$)COOCH$_3$ | solid |
| 1.155 | 4-Cl | 3-Cl | —CH(CH$_3$)COOC$_2$H$_5$ | oil |
| 1.156 | 4-Cl | 3-Cl | —CH(C$_2$H$_5$)COOC$_2$H$_5$ | oil |
| 1.157 | 4-Cl | 3-Cl | —CH$_2$—CN | m.p. 90–93° |
| 1.158 | 4-Cl | 3-Cl | —CH$_2$—C≡CH | solid |
| 1.159 | 4-Br | H | —C$_2$H$_5$ | solid |
| 1.160 | 4-Br | H | —C$_3$H$_7$(n) | solid |
| 1.161 | 4-Br | H | —CH$_2$—COOCH$_3$ | solid |
| 1.162 | 4-Br | H | —CH$_2$—COOC$_2$H$_5$ | m.p. ca. 40° |
| 1.163 | 4-Br | H | —CH(CH$_3$)COOCH$_3$ | oil |
| 1.164 | 4-Br | H | —CH(CH$_3$)COOC$_2$H$_5$ | oil |
| 1.165 | 4-Br | H | —CH(C$_2$H$_5$)COOC$_2$H$_5$ | oil |
| 1.166 | 4-Br | H | —CH$_2$—CH=CH$_2$ | m.p. 90–92° |
| 1.167 | 4-Br | H | —CH$_2$—CO—NH$_2$ | m.p. 147–149° |
| 1.168 | 4-Br | H | —CH(CH$_3$)—C≡CH | m.p. ca. 50° |
| 1.169 | 4-Br | H | —CH$_2$—COOC$_3$H$_7$(iso) | solid |
| 1.170 | 4-Br | H | —CH(CH$_3$)—COOC$_3$H$_7$(iso) | oil |
| 1.171 | 4-Br | H | —CH$_2$—CH=CH—CH$_3$ | oil |
| 1.172 | 4-Br | H | —CH$_2$—CONH—C$_6$H$_3$Cl$_2$(3,4) | m.p. 152–155° |

There are obtained analogously also the following compounds of the formula

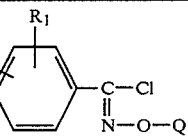

| Comp. No. | R₁ | R₂ | Q | |
|---|---|---|---|---|
| 1.173 | H | H | —CH$_2$—CN | oil |
| 1.174 | H | H | —CH$_2$—CO—NH$_2$ | oil |
| 1.175 | 4-Cl | H | —CH$_2$—CO—NH$_2$ | oil |
| 1.176 | H | H | —CH$_2$—COOCH$_3$ | |
| 1.177 | H | H | —CH$_2$—COOC$_2$H$_5$ | |
| 1.178 | H | H | —CH$_2$—COO(i-C$_3$H$_7$) | |
| 1.179 | 4-CH$_3$ | H | —CH(CH$_3$)COOCH$_3$ | |
| 1.180 | 4-Cl | H | —CH$_2$—COO(i-C$_3$H$_7$) | |
| 1.181 | 4-Cl | 2-Cl | —CH$_2$—COOCH$_3$ | |
| 1.182 | 4-Cl | 2-Cl | —CH$_2$—COOC$_2$H$_5$ | |
| 1.183 | 4-Cl | 3-Cl | —CH$_2$—COOCH$_3$ | |
| 1.184 | 4-Cl | 3-Cl | —CH$_2$—COOC$_2$H$_5$ | |
| 1.185 | 4-Cl | | —CH(CH$_3$)—COOC$_2$H$_5$ | |
| 1.186 | 4-CH$_3$O— | H | —CH$_2$—COOC$_2$H$_5$ | |
| 1.187 | H | H | —CH$_2$—C≡CH | oil |
| 1.188 | H | H | —CH$_2$—CON(CH$_3$)$_2$ | |
| 1.189 | 4-CH$_3$ | H | —nC$_3$H$_7$ | |
| 1.190 | 4-CH$_3$O | H | —CH$_3$ | |
| 1.191 | H | H | —CH$_2$—CONHC≡CH | oil |
| 1.192 | 4-Br | H | —CH$_2$—C≡CH | |
| 1.193 | H | H | —CH$_2$—CON(CH$_3$)—C$_2$H$_5$ | |
| 1.194 | H | H | —CH$_2$—CON(CH$_3$)—CH$_2$—CH=CH$_2$ | oil |
| 1.195 | 4-Cl | H | —CH$_2$—C≡CH | |
| 1.196 | 4-Cl | 2-Cl | —CH(CH$_3$)—C≡CH | |
| 1.197 | 3-CF$_3$ | H | —CH$_2$—COOC$_2$H$_5$ | |
| 1.198 | 3-CF$_3$ | H | —CH$_2$—HC=CH$_2$ | |
| 1.199 | H | H | —CH$_2$—CONH—CH$_2$—CH=CH$_2$ | oil |
| 1.200 | 3-CF$_3$ | H | —CH(CH$_3$)—COOC$_2$H$_5$ | |
| 1.201 | 4-NO$_3$ | H | —CH$_2$—CO—NH$_2$ | oil |
| 1.202 | H | H | 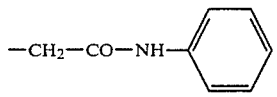 —CH$_2$—CO—NH— (phenyl) | oil |

-continued

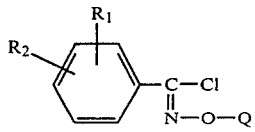

| Comp. No. | R₁ | R₂ | Q | |
|---|---|---|---|---|
| 1.203 | 4-Cl | H | $-CH(CH_3)-COOCH_3$ | oil |
| 1.204 | 4-NO₂ | H | $-CH_2COOCH_3$ | solid |
| 1.205 | H | H | $-CO-CH_2-NH_2$ | |
| 1.206 | 3-CF₃ | 5-CF₃ | $-CH_2-COOCH_3$ | |
| 1.207 | 2-CH₃ | H | $-CH_2-CN$ | oil |
| 1.208 | 2-F | H | $-CH_2-CN$ | oil |
| 1.209 | 2-F | H | $-CH_2-CONH_2$ | oil |
| 1.210 | 2-CH₃ | H | $-CH(CH_3)-COOCH_3$ | |
| 1.211 | 4-nC₄H₉O | H | $-CH_2-CN$ | oil |
| 1.212 | 4-isoC₃H₇O | H | $-CH_2-CO-NH_2$ | oil |
| 1.213 | 2-CH₃ | H | $-CH_2-CO-NH_2$ | oil |
| 1.214 | 3-NO₂ | H | $-CH_2-CO-NH_2$ | oil |
| 1.215 | 3-NO₂ | H | $-SO_2-CH_3$ | |
| 1.216 | 2-CH₃ | 4-CH₃ | $-CH_2-CH=CH_2$ | |

There are obtained analogously also the following compounds of the formula 25

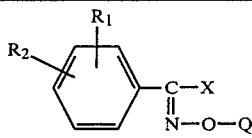

| Comp. No. | R₁ | R₂ | X | Q | |
|---|---|---|---|---|---|
| 1.217 | H | H | $-COCH_3$ | $-CH_2-CN$ | oil |
| 1.218 | H | H | $-COCH_3$ | $-CH_2-CO-NH_2$ | oil |
| 1.219 | H | H | $-COCH_3$ | $-CH_2-COOCH_3$ | oil |
| 1.220 | H | H | $-COCH_3$ | $-CH(CH_3)-COOCH_3$ | |
| 1.221 | 4-Cl | H | $-COCH_3$ | $-CH_2-CN$ | |
| 1.222 | 4-CH₃ | 2-CH₃ | $-COCH_3$ | $-CH_2-CN$ | |
| 1.223 | 3-CF₃ | H | $-COCH_3$ | $-CH_2-CO-NH_2$ | |
| 1.224 | 4-Cl | 2-NO₂ | $-COCH_3$ | $-CH_2-COOCH_3$ | |
| 1.225 | H | H | $-COCH_3$ | $-C_2H_5$ | |
| 1.226 | H | H | $-COCH_3$ | $-CH_2-CH=CH_2$ | |
| 1.227 | H | H | $-COOC_2H_5$ | $-CH_2-CN$ | oil |
| 1.228 | H | H | $-COOC_2H_5$ | $-CH_2-C\equiv CH$ | |
| 1.229 | H | H | $-COOC_2H_5$ | $-CH_2-CO-NH_2$ | |
| 1.230 | H | H | $-COOC_2H_5$ | $-CH_2-CO-N(CH_3)_2$ | |
| 1.231 | H | H | $-COOC_2H_5$ | $-CH_3$ | oil |
| 1.232 | H | H | $-NO_2$ | $-CH_2-CN$ | oil |
| 1.233 | H | H | $-NO_2$ | $-CH_2-COCH_2$ | oil |
| 1.234 | H | H | $-NO_2$ | $-CH_2-CONH-C_3H_7(n)$ | |
| 1.235 | H | H | $-NO_2$ | $-SO_2-\underset{}{\bigcirc}-CH_3$ | |
| 1.236 | H | H | $-NO_2$ | $-CH_2-SO_2N(CH_3)_2$ | |
| 1.237 | H | H | $-NO_2$ | $-CH_2-COOC_2H_5$ | |
| 1.238 | H | H | $-NO_2$ | $-CH(CH_3)-COOCH_3$ | |
| 1.239 | H | H | $-CO-NHCH_3$ | $-CH_2-CN$ | oil |
| 1.240 | H | H | $-CO-NHCH_3$ | $-CH_2-CO-NHCH_3$ | |
| 1.241 | H | H | $-CO-NHCH_3$ | $-CH_3$ | |
| 1.242 | H | H | $-CO-NHCH_3$ | $-CH_2-C\equiv CH$ | oil |
| 1.243 | H | H | $-CH_3$ | $-CH_2-CN$ | |
| 1.244 | H | H | $-CH_3$ | $-CH_2-CO-NH_2$ | oil |
| 1.245 | H | H | $-CH_3$ | $-CH_2-COOCH_3$ | |
| 1.246 | H | H | $-CH_3$ | $-CH(CH_3)-COO(iC_3H_7)$ | |
| 1.247 | H | H | $-CH_3$ | $-CH_2-CO-NH-CH_3$ | |
| 1.248 | H | H | $-CH_3$ | $-CH_2-CONH-CH_2C\equiv CH$ | |
| 1.249 | H | H | $-CH_3$ | $-CH_2-CONH-CH_2-CH=CH_2$ | |
| 1.250 | H | H | $-CH_3$ | $-CH_2-CH=CH_2$ | |
| 1.251 | 2-F | H | $-CH_3$ | $-CH_2-COOC_2H_5$ | |

-continued

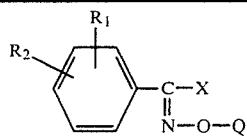

| Comp. No. | R₁ | R₂ | X | Q |
|---|---|---|---|---|
| 1.252 | 2-CH$_3$ | 5-CH$_3$ | —CH$_3$ | —CH$_2$—CH$_2$—O—CH$_3$ |
| 1.253 | H | H | —COOCH$_3$ | —CH$_2$—CN |
| 1.254 | 3-NO$_2$ | H | —COOCH$_3$ | —CH$_2$—COOCH$_3$ |
| 1.255 | H | H | —COOCH$_3$ | —CH$_2$—CO—NH$_2$ |
| 1.256 | H | H | —COOCH$_3$ | —CH$_3$ |
| 1.257 | H | H | —COOCH$_3$ | —nC$_5$H$_{11}$ |
| 1.258 | H | H | —COOCH$_3$ | —CH$_2$—CON(allyl)$_2$ |
| 1.259 | H | H | —COOCH$_3$ | —CH(CH$_3$)—COOCH$_3$ |
| 1.260 | H | 2-Cl | —COOCH$_3$ | —CH$_2$—CN |
| 1.261 | 4-Cl | 3-Cl | —COOCH$_3$ | —CH$_2$—COOCH$_3$ |
| 1.262 | 2-Cl | 2-NO$_2$ | —COOCH$_3$ | —CH$_2$—CN |
| 1.263 | 2-Cl | 2-NO$_2$ | —COOCH$_3$ | —CH$_2$—CN |
| 1.264 | H | H | H | —CH$_2$—CN |
| 1.265 | H | H | H | —CH$_2$—CONH$_2$ |
| 1.266 | H | H | —CO—CH$_2$C≡CH | |
| 1.267 | H | H | —CO—CH$_2$C≡CH | —CH$_2$—CN |
| 1.268 | H | H | —CO—CH$_2$C≡CH | —CH$_2$—CO—NH$_2$ |
| 1.269 | H | H | —CO—CH$_2$C≡CH | —CH$_2$—CO—NHCH$_3$ |
| 1.270 | H | H | —CO—CH$_2$C≡CH | —CH$_2$—CH=CH$_2$ |
| 1.271 | H | H | —CO—CH$_2$C≡CH | —CH$_3$ |
| 1.272 | H | H | —CO—NH$_2$ | —CH$_2$—CN |
| 1.273 | H | H | —CO—NH$_2$ | —CH$_2$—CO—NH$_2$ |
| 1.274 | H | H | Br | —CH$_2$—CN |
| 1.275 | H | H | Br | —CH$_2$—CO—NH$_2$ |
| 1.276 | H | H | Cl | —CH$_2$—CH$_2$—CN |
| 1.277 | H | H | —COCH$_3$ | —CH$_2$—CH$_2$—CN |
| 1.278 | H | H | —COOCH$_3$ | —CH$_2$—CH$_2$—CN |
| 1.279 | H | H | —CONH$_2$ | —CH$_2$—CH$_2$—CN |

Similarly important products are the compounds derived from naphthylglyoxylonitrile and from analogous derivatives; for example compounds of the formula

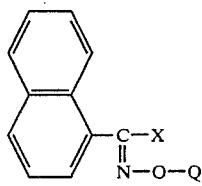

| Comp. No. | X | Q | |
|---|---|---|---|
| 2.1 | —CN | —CH$_2$—CN | m.p. 81–82° |
| 2.2 | —CN | —CH$_2$—CO—NH$_2$ | semisolid |
| 2.3 | —CN | —CH(CH$_3$)—C≡CH | oil |
| 2.4 | —CN | —CH$_2$—C≡CH | oil |
| 2.5 | —CN | —CH$_2$—CH=CH$_2$ | oil |
| 2.6 | —CN | —CH$_3$ | oil |
| 2.7 | —CN | —C$_2$H$_5$ | oil |
| 2.8 | —CN | n-C$_3$H$_7$ | oil |
| 2.9 | —CN | —CH$_2$—COOCH$_3$ | semisolid |
| 2.10 | —CN | —CH$_2$—COOC$_2$H$_5$ | oil |
| 2.11 | —CN | —CH(CH$_3$)—COOCH$_3$ | oil |
| 2.12 | —CN | —CH(CH$_3$)—COOC$_2$H$_5$ | oil |
| 2.13 | —CN | —CH(C$_2$H$_5$)—COOC$_2$H$_5$ | |
| 2.14 | —CN | —CO—C$_6$H$_5$ | m.p. 115–118° |
| 2.15 | —CN | —SO$_2$—⟨C$_6$H$_4$⟩—Cl | |
| 2.16 | —CN | —SO$_2$—CH$_3$ | |
| 2.17 | —CN | —CH(CH$_3$)—COO(isoC$_3$H$_7$) | oil |

-continued

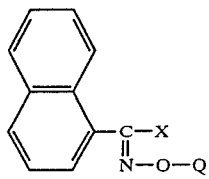

| Comp. No. | X | Q | |
|---|---|---|---|
| 2.18 | —CN | —CH(CH₃)—CON(C₂H₅)₂ | oil |
| 2.19 | —CN | —CH₂—COO(isoC₃H₇) | oil |
| 2.20 | —CN | —CH₂—CO—NH—(3,4-Cl₂C₆H₃) | |
| 2.21 | —CN | —CO—NH—CH₃ | |
| 2.22 | —Cl | —CH₂—CN | viscous |
| 2.23 | —Cl | —CH₂—CO—NH₂ | oil |
| 2.24 | —Cl | —C₂H₅ | |
| 2.25 | —Br | —CH₂—COOtert.C₄H₉ | |
| 2.26 | —Cl | —CH(CH₃)—COOCH₃ | |
| 2.27 | —COCH₃ | —CH₂—CN | oil |
| 2.28 | —COCH₃ | —CH₂—CO—NH₂ | oil |
| 2.29 | —COCH₃ | —CH₂—COOCH₃ | |
| 2.30 | —COCH₃ | —CH₂—CH(Cl)—CH₂Cl (gem-diCl on central C) | |
| 2.31 | —COCH₃ | —CH₂—C≡CH | |
| 2.32 | —COCH₃ | —CH₃ | oil |
| 2.33 | —COOCH₃ | —CH₂—CN | oil |
| 2.34 | —COOCH₃ | —CH₂—CO—NH₂ | |
| 2.35 | —C₂H₅ | —CH₂—CN | |
| 2.36 | —CO—NH₂ | —CH₂—CO—NH₂ | |
| 2.37 | —CH₃ | —CH₂—CO—NH—(3,4-Cl₂C₆H₃) | oil |
| 2.38 | —Cl | —CH₂—CO—NH—(3,4-Cl₂C₆H₃) | |
| 2.39 | —CN | —CH₂—CH=CH—CH₃ | oil |
| 2.40 | —CN | —CH₂—CONH—CH₃ | oil |
| 2.41 | —CN | —CH₂—CON(CH₃)₂ | oil |
| 2.42 | —CN | —CH₂—CONH—CH₂—CH=CH₂ | oil |
| 2.43 | —Cl | —CH₂—CONH—CH₂—C≡CH | oil |
| 2.44 | —Cl | —CH₂—CONH—CH₃ | oil |
| 2.45 | —COCH₃ | —CH₂—CONH—CH₃ | oil |
| 2.46 | —COCH₃ | —CH₂—CON(CH₃)—C₂H₅ | oil |
| 2.47 | —COOCH₃ | —CH₂—CONH—CH₃ | oil |
| 2.48 | —COOCH₃ | —CH₂—COOCH₃ | oil |
| 2.49 | —COOCH₃ | —CH₂—C≡CH | oil |
| 2.50 | —NO₂ | —CH₂—CN | oil |
| 2.51 | —NO₂ | —CH₂—CO—NH₂ | oil |

Also the following groups of heterocyclic oxime derivatives are obtained in an analogous manner.

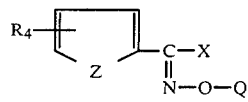

| Comp. No. | R4 | X | Z | Q | |
|---|---|---|---|---|---|
| 3.1 | H | —CN | S | —CH2—CN | oil |
| 3.2 | H | —CN | S | —CH2—CONH2 | |
| 3.3 | H | —CN | S | —CH2—COOCH3 | |
| 3.4 | H | —CN | S | —CH(CH3)—COOCH3 | |
| 3.5 | 5-Cl | —CN | S | —CH2—CN | |
| 3.6 | 5-Cl | —CN | S | —CH2—CONH2 | |
| 3.7 | 5-Cl | —CN | S | —CH2—COOC2H5 | |
| 3.8 | 5-Cl | —CN | S | —CH(CH3)—COOCH3 | |
| 3.9 | 5-Cl | —CN | S | —CH(CH3)—COO(isoC3H7) | |
| 3.10 | 5-Cl | —CN | S | —CH2—C≡CH | |
| 3.11 | H | —CN | S | —CH2—CH=CH2 | |
| 3.12 | H | —CN | S | —CH2—COO(isoC3H7) | |
| 3.13 | H | —CN | S | —C2H5 | |
| 3.14 | H | —CN | S | —CH2—CH2—O—CH3 | |
| 3.15 | H | —CH3 | S | —CH2—CN | |
| 3.16 | H | —CH3 | S | —CH2—CONH2 | |
| 3.17 | H | —CH3 | S | —CH2—COOCH3 | |
| 3.18 | H | —CH3 | S | —CH(CH3)—COOCH3 | |
| 3.19 | H | —CH3 | S | —CH2—C≡CH | oil |
| 3.20 | H | —CH3 | S | —CH2—CH=CH2 | |
| 3.21 | H | —CH3 | S | —CH2—COO(isoC3H7) | |
| 3.22 | H | —CH3 | S | —C2H5 | |
| 3.23 | H | —CH3 | S | —CH2—CH2—O—CH3 | |
| 3.24 | H | —CN | O | —CH2—CN | oil |
| 3.25 | H | —CN | O | —CH2—CO—NH2 | viscous |
| 3.26 | H | —CN | O | —CH2—COOCH3 | |
| 3.27 | H | —CN | O | —nC3H7 | |
| 3.28 | H | —CN | O | —CH2—CH=CH2 | |
| 3.29 | H | —CN | O | —CH2—C≡CH | |
| 3.30 | H | —CN | O | —CH2—CH2—O—CH3 | |
| 3.31 | H | —CN | O | —CO—NH—CH3 | oil |
| 3.32 | H | —CN | O | —CO—NH—CH2—C≡CH | solid |
| 3.33 | H | —CN | O | —CO—NH—(3,4-dichlorophenyl) | |
| 3.34 | 5-NO2 | —CN | O | —CH2—CN | oil |
| 3.35 | 5-Cl | —CN | O | —CH2—CN | oil |
| 3.36 | H | —CH3 | O | —CH2—CN | oil |
| 3.37 | H | —CH3 | O | —CH2—CO—NH2 | oil |
| 3.38 | H | —CH3 | O | —CH2—COO(iC3H7) | |
| 3.39 | H | —NO2 | O | —CH2—CN | oil |
| 3.40 | H | Cl | O | —CH2—CN | oil |
| 3.41 | H | Cl | O | —CH2—CONH2 | oil |
| 3.42 | H | Cl | S | —CH2—CN | oil |
| 3.43 | H | Cl | S | —CH2—CONH2 | oil |
| 3.44 | 4-CH3 | —CH3 | O | —CH(CH3)—COOCH3 | |

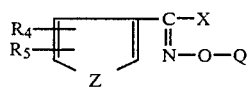

| Comp. No. | R4 | R5 | X | Z | Q | |
|---|---|---|---|---|---|---|
| 3.45 | H | H | —CN | S | —CH2—CN | oil |
| 3.46 | H | H | —CN | S | —CH2—CO—NH2 | oil |
| 3.47 | H | H | —CN | S | —CH2—COOCH3 | |
| 3.48 | H | H | —CN | S | —C2H5 | |
| 3.49 | H | H | —CN | S | —CO—C2H5 | |
| 3.50 | H | H | —CN | S | —SO2—CH3 | |
| 3.51 | H | H | —CN | S | —CH2—C(Cl)=CH2 | |
| 3.52 | H | H | —CN | S | —CH2—CON(C3H7)2 | solid |
| 3.53 | 2-Cl | 5-Cl | —CN | S | —CH2—CN | oil |
| 3.54 | 2-Cl | 5-Cl | —CN | S | —CH2—CO—NH2 | oil |

-continued

| | | | | | | |
|---|---|---|---|---|---|---|
| 3.55 | 5-NO2 | H | —CN | O | —CH2—CN | oil |
| 3.56 | H | H | CH3 | O | —CH2—CN | oil |
| 3.57 | H | H | CH3 | O | 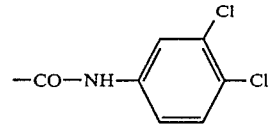 | solid |
| 3.58 | H | H | —COCH3 | O | —CH2—COOCH3 | |
| 3.59 | H | H | —COCH3 | O | —CH(CH3)—COOCH3 | |
| 3.60 | H | H | —NO2 | O | —SO2—CH3 | |
| 3.61 | H | H | Cl | O | —CH2—CN | oil |
| 3.62 | H | H | Cl | O | —CH2—CO—NH2 | oil |
| 3.63 | H | H | Cl | O | —CH2—CONH—C2H5 | solid |
| 3.64 | H | H | Cl | S | —CH2—CN | oil |
| 3.65 | H | H | —CONH2 | O | —CH2—CO—NH2 | oil |
| 3.66 | H | H | —COOCH3 | O | —CH2—COOCH3 | oil |

A further important individual group having an action influencing plant growth and protecting plants is that of the following dephenyl ether derivatives of the formula:

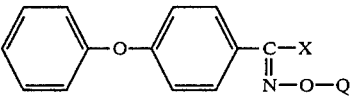

| Comp. No. | X | Q |
|---|---|---|
| 4.1 | —CN | —CH2—CN |
| 4.2 | —CN | —CH2—CO—NH2 |
| 4.3 | —CN | —CH2—COO—CH3 |
| 4.4 | —CN | —CH(CH3)—COO—CH3 |
| 4.5 | —CN | —CH(CH3)—COO—C2H5 |
| 4.6 | —CN | —CH3 |
| 4.7 | H | —CH2—CN |
| 4.8 | H | —CH2—CO—NH2 |
| 4.9 | H | —CH2—COO—CH3 |
| 4.10 | CH3 | —CH2—CN |
| 4.11 | CH3 | —CH(CH3)—COOCH3 |
| 4.12 | C2H5 | —CH2—COOC2H5 |
| 4.13 | Cl | —CH2—CN |
| 4.14 | Cl | —CH2—CO—NH2 |
| 4.15 | Cl | —C2H5 |
| 4.16 | Cl | —CH2—CH=CH2 |
| 4.17 | NO2 | —CH2—CN |
| 4.18 | NO2 | —CH2—C≡CH |
| 4.19 | NO2 | —CO—NH—CH3 |
| 4.20 | —CO—CH3 | —CH2—COO(isoC3H7) |
| 4.21 | —CO—CH3 | 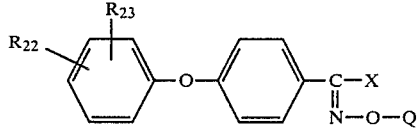 |
| 4.22 | —CO—CH3 | —CH2—CO—NH2 |
| 4.23 | —CN | —CH2—CONH—CH3 |
| 4.24 | —CO—NH2 | —CH2—CO—NH2 |
| 4.25 | —CO—OCH3 | —CH2—CN |
| 4.26 | —CO—OCH3 | —CH2—COOC2H5 |
| 4.27 | —CO—OCH3 | —C2H5 |
| 4.28 | —CO—OCH3 | —CH2—C≡CH |

A group of compounds which in the case of high applied amounts of 6 kg per hectare and more can shift the plant-growth regulating action in the direction of a herbicidal action, but which is low applied amounts of 1 kg per hectare (and below) are completely tolerated by the crops, without the said compound losing their properties for regulating plant growth and for protecting plants, is that of the following substituted diphenyl ether derivatives of the formula I:

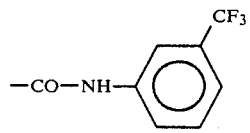

| Comp. No. | R22 | R23 | X | Q |
|---|---|---|---|---|
| 5.1 | 4-Cl | 2-Cl | —CN | —CH2—CO—NH2 |
| 5.2 | 4-Cl | 2-Cl | —CN | —CH2—COOCH3 |
| 5.3 | 4-Cl | 2-Cl | —CN | —CH(CH3)—COOCH3 |
| 5.4 | 4-Cl | 2-CN | —CN | —CH2—COOCH3 |
| 5.5 | 4-Cl | 2-CN | —CN | —CH(CH3)—COOCH3 |
| 5.6 | 4-CF3 | 2-Cl | —CN | —CH(CH3)—COOCH3 |
| 5.7 | 4-CF3 | 2-Cl | —CN | —CH2—COOC2H5 |
| 5.8 | 4-NO2 | H | —CN | —CH(CH3)—COOCH3 |
| 5.9 | 4-Cl | 2-Cl | —Cl | —CH2—CN |
| 5.10 | 4-Cl | 2-Cl | —Cl | —CH2—COOCH3 |
| 5.11 | 4-Cl | 2-Cl | —Cl | —CH(CH3)—COOCH3 |
| 5.12 | 4-Cl | 2-Cl | —CH3 | —CH2—COOCH3 |
| 5.13 | 4-Cl | 2-Cl | —CH3 | —CH(CH3)—COOCH3 |
| 5.14 | 4-Cl | 2-Cl | H | —CH2—COOCH3 |
| 5.15 | 4-Cl | 2-Cl | H | —CH(CH3)—COOCH3 |
| 5.16 | 4-CF3 | 2-Cl | H | —CH2—COOCH3 |
| 5.17 | 4-CF3 | 2-Cl | H | —CH(CH3)—COOCH3 |

The compounds of the formula I can be used on their own or together with the active substances to be antagonised, and also together with suitable carriers and-/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commerical compositions is between 0.01 and 90%.

For application, the compounds of the formula I can be in the following forms (the weight-percentage figures in brackets signify advantageous amounts of active substance):

solid preparations:
  dusts and scattering agents (up to 10%), granulates [coated granules, impregnated granules and homogeneous granules] and pellets (1 to 80%);

liquid preparations:
  a. water-dispersible concentrates of active substance: wettable powders and pastes (25 to 90% in the commercial packing, 0.01 to 15% in ready-for-use solutions); emulsion concentrates and solution concentrates 10 to 50%, 0.01 to 15% in ready-for-use solutions);

b. solutions (0.1 to 20%), e.g. for dressing, aerosols.

The active substances of the formula I of the present invention can be formulated for example as follows.

Dust: The following substances are used to produce (a) a 5% dust and (b) a 2% dust:

5 parts of active substance,
95 parts of talcum;
2 parts of active substance,
1 part of highly dispersed silicic acid, and
97 parts of talcum.

The active substances are mixed and ground with the carriers, and in this form they can be applied by dusting.

Granulate: The following substances are used to produce a 5% granulate:

5 parts of active substance,
0.25 part of epichlorohydrin,
0.25 part of cetyl polyglycol ether,
3.50 parts of polyethylene glycol, and
91 parts of kaolin (particle size 0.3–0.8 mm).

The active substance is mixed with epichlorohydrin and dissolved in 6 parts of acetone; the polyethylene glycol and cetyl polyglycol ether are then added. The solution thus obtained is sprayed onto kaolin, and the acetone is subsequently evaporated off in vacuo. A microgranulate of this kind can be advantageously worked into seed furrows.

Wettable powder: The following constituents are used to produce (a) a 70% wettable powder, (b) a 40% wettable powder, (c) and (d) a 25% wettable powder, and (c) a 10% wettable powder:

a.

70 parts of active substance,
5 parts of sodium dibutylnaphthylsulphonate,
3 parts of naphthalenesulphonic acid/phenolsulphonic acid/formaldehyde condensate 3:2:1,
10 parts of kaolin, and
12 parts of Champagne chalk;

b.

40 parts of active substance,
5 parts of sodium lignin sulphonate,
1 part of sodium dibutylnaphthalenesulphonate, and
54 parts of silicic acid;

c.

25 parts of active substance,
4.5 parts of calcium lignin sulphonate,
1.9 parts of Champagne chalk/hydroxyethylcellulose mixture (1:1),
1.5 parts of sodium dibutylnaphthalenesulphonate,
19.5 parts of silicic acid,
19.5 parts of Champagne chalk, and
28.1 parts of kaolin;

d.

25 parts of active substance,
2.5 parts of isooctylphenoxy-polyoxyethylene-ethanol,
1.7 parts of Champagne chalk/hydroxyethylcellulose mixture (1:1),
8.3 parts of sodium aluminium silicate,
16.5 parts of kieselguhr, and
46 parts of kaolin; and e.

10 parts of active substance,
3 parts of a mixture of the sodium salts of saturated fatty alcohol sulphates,
5 parts of naphthalenesulphonic acid/formaldehyde condensate, and
82 parts of kaolin.

The active substances are intimately mixed in suitable mixers with the additives, and the mixture is then ground in the appropriate mills and rollers. There are obtained wettable powders which have excellent wetting and suspension properties, which can be diluted with water to give suspensions of the desired concentration, and which can be used in particular for leaf application, for seed dressing or for the immersion treatment of seedlings Emulsifiable concentrate: The following substances are used to produce a 25% emulsifiable concentrate:

25 parts of active substance,
2.5 parts of epoxidised vegetable oil,
10 parts of an alkylarylsulphonate/fatty alcohol polyglycol ether mixture,
5 parts of dimethylformamide, and
57.5 parts of xylene.

Emulsions of the desired concentration can be prepared from these concentrates by dilution with water; and these emulsions are particularly suitable for seed dressing.

Biological Examples

In order to determine the selective herbicidal action of a highly effective herbicidal leading product of the chloroacetanilidine class, on its own and together with the antidote of the formula I according to the invention, the following tests were carried out; the herbicidal active substance used in the tests was N-[3'-methoxy-propyl-(2')]-2-methyl-6-ethyl-chloroacetanilide (substance H) (German Offenlegungsschrift No. 2,328,340).

1. Pre-emergence application as a tank mixture a. After sowing

Aqueous suspensions were produced from formulated wettable powders of the herbicide (substance H) and from an antidote of the formula I (substance S) according to the invention; and these were then applied, singly and also as mixtures in amounts of 1 kg to 8 kg/hectare with mixture ratios H:S of 4:1 to 1:4, after the sowing of various varieties of cultivated millet of the Sorghum hybridum type (varieties "Funk", "Dekalb", "NK 222" and "DC 59"), in pots or in seed trays in a greenhouse, the said suspensions being applied to the surface of the soil in the sown vessels. The vessels were then kept at 22°–23° C. with customary watering. The results were evaluated after 15 days on the basis of the following linea scale:

9 = plants undamaged (as untreated control plants)
1 = plants completely destroyed,
2 to 8 = intermediate stages of damage.

b. Before sowing (PPI)

In the same manner as under (a), soil in pots and in seed trays was treated with the liquors containing the active substance, and immediately afterwards these vessels were sown with seeds of the millet variety "Funk".

Whereas the compound H when used alone in the given applied amounts damages or destroys the cultivated millet, its effect when an antidote of the formula I is present is neutralised either completely or to a great extent. This is achieved in particular with the compounds Nos. 1.1, 1.4, 1.14, 1.20 and 1.34.

2. Seed dressing (wet)

Aqueous emulsion concentrates of an antidote of the formula I were prepared, and each shaken in a bottle with 50 g of cultivated millet seed. The various concentrations of antidote amounted to between 20 and 150 g of antidote per 100 kg of seed. Shortly after the dressing treatment, the seed was sown in seed trays and treated in the customary manner with spray liquors of the herbicide H as described under 1(a). The results were evaluated 15 days after application of the herbicide using the same ratings as before.

The results showed here too that protection of the cultivated millet is obtained where the concentration of herbicide is low, but sufficiently high to combat weeds, as a consequence of the antidote S. The following compounds were particularly effective as antidotes: Nos. 1.1, 1.4, 1.14, 1.20, 1.34, 1.44, 1.70 to 1.75, 1.78, 1.82, 1.91, 1.98, 1.103, 1.108, 1.110, 1.126, 1.139, 1.173, 1.174, 1.177, 1.188, 1.191, 1.199, 1.204, 1.207 to 1.209, 1.217, 1.218, 1.227, 1.230, 1.239, 1.240, 1.253, 1.255, 1.267, 1.274, 1.275 to 1.279, and others. Compounds of the U.S. Patent Specification No. 3,799,757 did not act as antidotes.

The antagonistic action of an antidote of the formula I does not extend as a rule to the main weeds, such as Echinochloa, Setaria italica, etc., which are destroyed practically to the same extent as they are when the antidote is not present.

Similarly good antidote effects are achieved also with other chloroacetanilides and thiolcarbamates, and also on other cultivated crops, such as rice, maize, wheat, cotton, soya bean or sugar cane.

Increase in yield of soya bean crops

In a field of soya bean plants of the "Lee 68" variety, plots each 50 square meters in size were sprayed with aqueous preparations of an active substance of the formula I when the plants were in the 5–6-leaf stage. The amount of active substance applied was 500 g per hectare. At the point of time of harvesting, it was established that untreated plants were for the most part broken (flattened), whilst on the treated plots all the plants were standing upright and displaying better pod setting. Compared with the control plots, the treated plots gave approximately 10–15% higher yields.

Significant increases in yield of 12% or more were achieved on plots which had been treated with the compounds Nos. 1.1, 1.3, 1.4, 1.167, or others.

Reduction of side shoots on tabacco crops

Tobacco plants were grown in a greenhouse and topped as blossoming was beginning. One day later they were sprayed with aqueous spray liquors of the active substances Nos. 1.106 and 1.148. The concentration of the active substances was 0.66 and 1.32% of active substance, respectively.

Whereas in the case of the untreated plants, strong side shoots developed from the leaf axil buds, the growth of side shoots on the treated tobacco plants remained greatly reduced. Similar results were obtained with other compounds of the formula I with a propargyl ether structure.

Bilogical tests under stress conditions

A. Plant growth at below optimum temperature

Rice plants in the 2- to 3-leaf stage were immersed with the roots and the lower part of the shoot for 45 minutes in a solution containing 10 ppm (=0.001%) of an active substance of the formula I. They were afterwards replanted in dripping wet soil in asbestos cement containers 70×70 cm in size, and kept at a temperature of only 18°–22° C. instead of at 28°–30° C. The surface of the soil in the containers was covered with 2-3 cm of water after 3 days. After a further 18 days, the treated plants were compared with the untreated control plants.

The rice plants treated with compounds of the formula I or Ia had a root system which was on average 30 to 50% larger. Compounds of the U.S. Patent Specification No. 3,799,757 showed no such action.

B. Plant development with slightly damaged seedlings

Rice seed which had been pre-germinated in a quartz sand nutrient solution was immersed with the formed slightly yellowish shoots for 45 minutes in a solution containing 10 ppm of an active substance of the formula I; they were then replanted, with 42 plants in each case, in an asbestos cement vessel as described under A, and subsequently kept, until the time for gathering, at the normal temperature of 28°–30° C. with the customary watering.

The final evaluation was with respect to dry weight of the parts of the plants above the soil, number of panicles and the dry grain weight compared with 42 correspondingly pre-germinated but untreated control plants. The following mean values were obtained from several test series.

|  | Control plants | Treated plants | Increase |
|---|---|---|---|
| dry weight: | 507 g | 762–820 g | 50.3 to 61.7% |
| number of panicles: | 242 | 284–352 g | 17.4 to 45.5% |
| dry grain weight: | 182 g | 220–290 g | 20.9 to 59.3% |

The compounds Nos. 1.1, 1.4, 1.35, 1.44, 1.49, 1.78, 1.88, 1.173, 1.174, 1.207, 1.208, 1.217, 1.218, 1.253, 1.276, 1.277, 1.278, 2.1 and 3.1 were distinguished in this series of tests by particularly high increases. Compounds from U.S. Patent Specification No. 3.799,757 produced no such effects. The seeds of other cultivated plants, such as maize, cereals, soya bean and cotton, can be pre-treated in a manner analogous to that described in the case of rice, and similar increases in yield are obtained.

I claim:

1. A compound of the formula

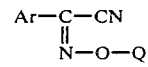

wherein Ar represents naphthyl or

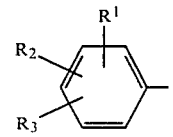

in which $R_1$ represents hydrogen, halogen, lower alkyl, lower alkoxy of phenoxy in the para-position which is optionally substituted a maximum of twice by halogen, cyano, nitro or trifluoromethyl, and each of $R_2$ and $R_3$ represents hydrogen, halogen, nitro, lower alkyl, trifluoromethyl or lower alkoxy, and Q is lower alkanecarboxylic acid ester in which the ester moiety has from 1 to 8 carbon atoms.

2. A compound according to claim 1 which is

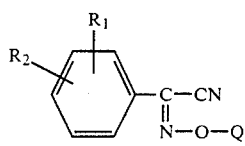

wherein
$R_1$ is hydrogen, lower alkyl, halogen or methoxy,
$R_2$ is hydrogen, chlorine or methyl, and
Q is lower alkanecarboxylic acid ester in which the ester moiety has from 1 to 4 carbon atoms.

3. A compound according to claim 1 which is

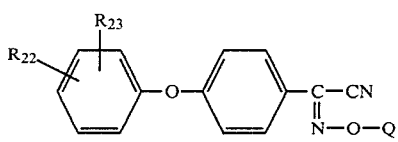

in which
$R_{22}$ is hydrogen, chlorine, trifluoromethyl or nitro,
$R_{23}$ is hydrogen, chlorine or cyano, and
Q is lower alkanecarboxylic acid ester in which the ester moeity has 1 or 2 carbon atoms.

4. The compound according to claim 3 which is

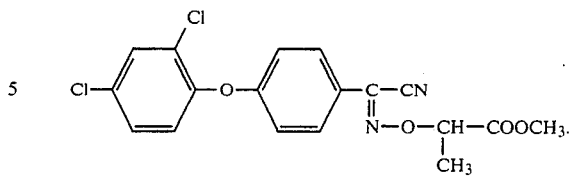

5. The compound according to claim 3 which is

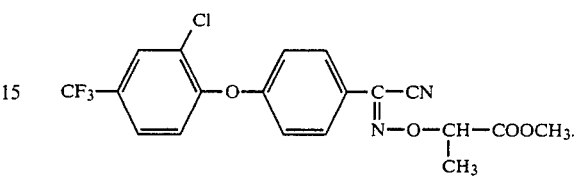

6. A compound according to claim 1 which is

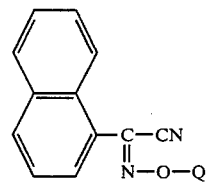

wherein Q is a lower alkanecarboxylic acid ester in which the ester moiety has from 1 to 3 carbon atoms.

* * * * *

UNITED STATES PATENT AND TRADEMARK OFFICE
CERTIFICATE OF CORRECTION

PATENT NO. : 4,518,536
DATED : May 21, 1985
INVENTOR(S) : Henry Martin

It is certified that error appears in the above-identified patent and that said Letters Patent is hereby corrected as shown below:

Claim 1, Column 36, Line 64 should read-- alkoxy or phenoxy in the para-position which is --.

Signed and Sealed this

First Day of October 1985

[SEAL]

Attest:

Attesting Officer

DONALD J. QUIGG

Commissioner of Patents and
Trademarks—Designate